US010768159B2

(12) United States Patent
Xie et al.

(10) Patent No.: US 10,768,159 B2
(45) Date of Patent: Sep. 8, 2020

(54) METHOD FOR TRACING WINE ORIGIN BASED ON MULTIELEMENTS AND STABLE ISOTOPES

(71) Applicants: FOOD INSPECTION CENTER OF CIQ-SHENZHEN, Shenzhen (CN); SHENZHEN ACADEMY OF INSPECTION AND QUARANTINE, Shenzhen (CN)

(72) Inventors: Liqi Xie, Shenzhen (CN); Hao Wu, Shenzhen (CN); Zhi Yan, Shenzhen (CN); Bo Chen, Shenzhen (CN); Xiaolei Jin, Shenzhen (CN); Baohui Jin, Shenzhen (CN); Xuehai Bian, Shenzhen (CN); Xu Zhao, Shenzhen (CN)

(73) Assignees: FOOD INSPECTION CENTER OF CIQ-SHENZHEN, Shenzhen, Guangdong (CN); SHENZHEN ACADEMY OF INSPECTION AND QUARANTINE, Shenzhen, Guangdong (CN)

(*) Notice: Subject to any disclaimer, the term of this patent is extended or adjusted under 35 U.S.C. 154(b) by 515 days.

(21) Appl. No.: 15/549,989

(22) PCT Filed: Sep. 5, 2016

(86) PCT No.: PCT/CN2016/098128
§ 371 (c)(1),
(2) Date: Aug. 9, 2017

(87) PCT Pub. No.: WO2017/211015
PCT Pub. Date: Dec. 14, 2017

(65) Prior Publication Data
US 2019/0064135 A1 Feb. 28, 2019

(30) Foreign Application Priority Data

Jun. 8, 2016 (CN) .......................... 2016 1 0404101

(51) Int. Cl.
*G01N 33/14* (2006.01)
*G01N 30/02* (2006.01)
(Continued)

(52) U.S. Cl.
CPC .......... *G01N 33/146* (2013.01); *G01N 30/02* (2013.01); *G01N 30/8675* (2013.01);
(Continued)

(58) Field of Classification Search
CPC ...... G01N 30/02; G01N 27/62; G01N 33/146; G01N 30/8675; G01N 33/143; G01N 2030/025; H01J 49/105
See application file for complete search history.

(56) References Cited

FOREIGN PATENT DOCUMENTS

| CN | 102455320 A | * | 5/2012 | ............. G01N 27/62 |
| CN | 102967668 A | * | 3/2013 | ............. G01N 30/02 |

* cited by examiner

*Primary Examiner* — Regis J Betsch
*Assistant Examiner* — Kaleria Knox
(74) *Attorney, Agent, or Firm* — Kolisch Hartwell, P.C.

(57) ABSTRACT

The present application provides a method for tracing wine origin based on multielements and stable isotopes, comprising the steps of:
1) collecting wine samples from a plurality of origins;
2) filtering the wine samples collected in step 1) and using the filtrate for carbon stable isotope ratio analysis of ethanol and glycerol; using the filtrate for analyzing oxygen stable isotopes in water; performing digestion with $HNO_3$ overnight, and diluting to a constant volume to be tested;
3) performing carbon stable isotope analysis, oxygen stable isotope ratio analysis and elemental analysis;
(Continued)

4) utilizing information of the origins of the wine samples and analytical data of step 3) to perform statistical modeling to obtain a wine origin discrimination model coefficient matrix and a corresponding predicted accuracy rate of the origin discrimination; and
5) determining attributes of the wine origin by using the statistical model.

5 Claims, 1 Drawing Sheet

(51) Int. Cl.
  *G01N 30/86* (2006.01)
  *H01J 49/10* (2006.01)
(52) U.S. Cl.
  CPC ..... *G01N 33/143* (2013.01); *G01N 2030/025* (2013.01); *H01J 49/105* (2013.01)

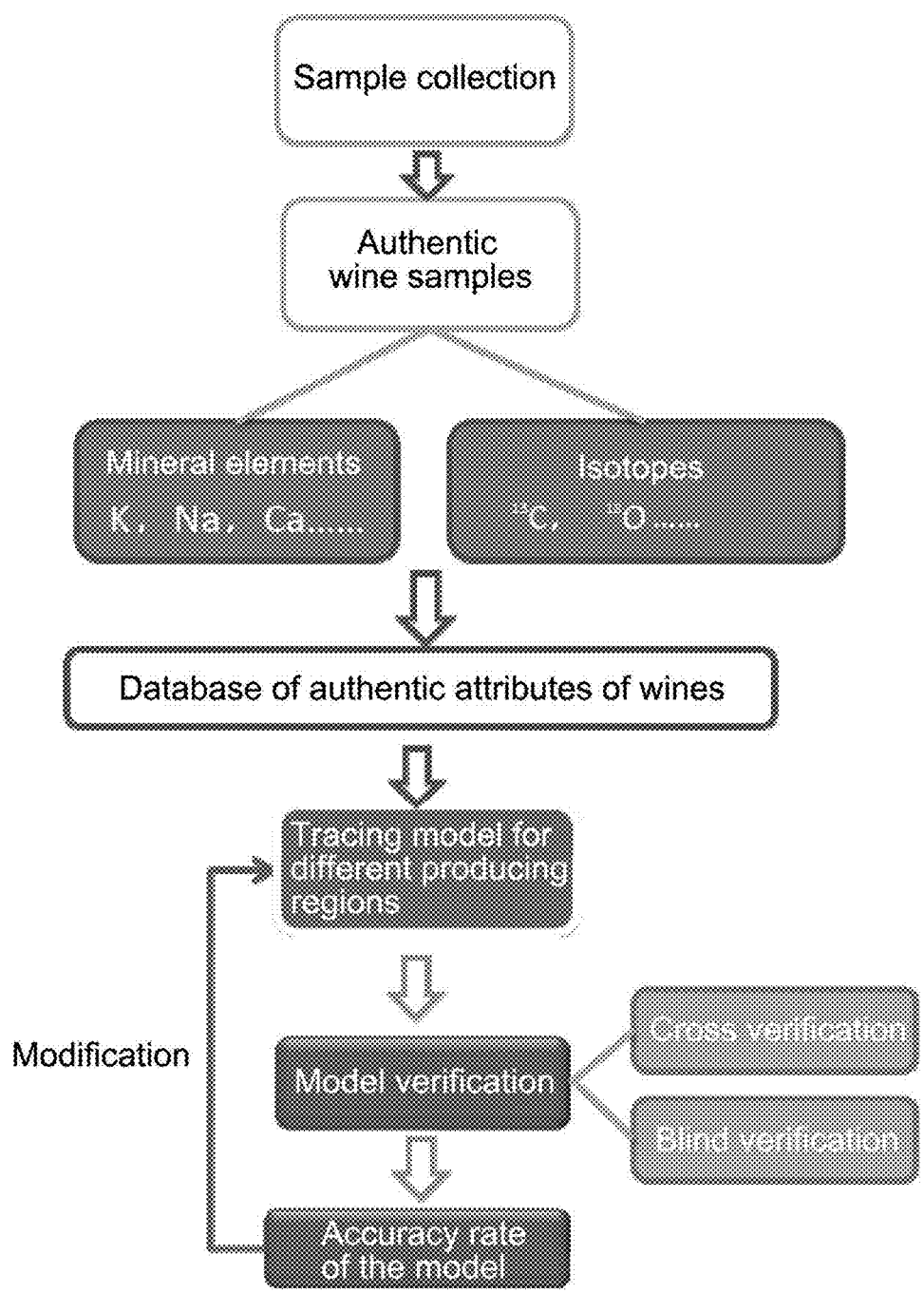

METHOD FOR TRACING WINE ORIGIN BASED ON MULTIELEMENTS AND STABLE ISOTOPES

TECHNICAL FIELD

The present invention relates to a method for tracing wine origin based on multielements and stable isotopes.

BACKGROUND ART

The statement made in this part only provides background information which relates to the contents disclosed in the present invention, and may not constitute the prior art.

Currently, there has been CN102967668A performing an identification and analysis of the origin of the wine based upon a method for identifying wine origin by a stable isotope ratio. However, this method only uses oxygen isotope as a tracing index, which cannot accurately determine the origin thereof, and has a limited applicability. There are also foreign journal literatures elucidating the principle of differentiating origins through elements and stable isotopes, but they are merely limited to the differentiation between sub-producing regions and have no practical value.

Firstly, the applicable area of the prior art is limited, and it is just applicable to a small region scope (e.g. the differentiation between origins within a region or within a country). Secondly, the existing technologies have relatively simplex indices for origins discrimination and have a low efficiency regarding the differentiation of origins and poor accuracy rate.

Thus, the prior art is to be improved and developed.

DISCLOSURE OF THE INVENTION

In order to solve the above-mentioned problems in the prior art, the present invention provides a method for tracing wine origin based on multielements and stable isotopes.

The method for tracing wine origin based on multielements and stable isotopes according to the present invention comprises the steps of:

1) sample collection: collecting wine samples from a plurality of origins, wherein the samples collected from each country are not less than 50 in number, and cover the main origins in this region respectively, and a distribution of the origins of authentic samples from different countries in the present invention are shown in Table 1.

2) sample pre-processing: filtering each of the wine samples collected in step 1) using a pore size of 0.22 μm aqueous filter membrane, and pouring 1.5 ml of a filtrate into an autosampler vial for carbon stable isotope ratio analysis of ethanol and glycerol; pouring 0.3 ml of the wine sample into a 12 ml glass tube with stopper for analyzing oxygen stable isotopes in the water; and pouring 0.5 ml of the wine sample into a 15 ml centrifuge tube, and adding 0.5 ml of concentrated $HNO_3$, performing digestion overnight, and diluting to 10 ml to be tested.

3) sample analysis: 1. carbon stable isotope analysis: switching the host machine of a stable isotope ratio mass spectrometer (Thermo Fisher, Delta V advantage) on and adjusting a reference gas balance, such that the variations of the carbon and oxygen stable isotope ratios of ten-group $CO_2$ reference gases are less than 0.06‰. GC conditions: ethanol: a sample injection amount of 0.1 μl, a sample injection port of 250° C., a carrier gas high pure helium, a flow rate of 1.5 ml/min, and a split ratio of 200:1. Programmed temperature-rising conditions: an initial temperature of 40° C., holding for 1 min, and then raising it to 220° C. at a rate of 50° C./min, holding for 3 min. Glycerol: a sample injection amount of 0.2 μl, a sample injection port temperature of 250° C., a carrier gas of high pure helium, a flow rate of 1.5 ml/min, and a split ratio of 20:1. Programmed temperature-rising conditions: an initial temperature of 80° C., holding for 1 min, and then raising it to 240° C. at a rate of 15° C./min, holding for 2 min. Isolink conditions: a combustion tube temperature of 1000° C., and switching the mass spectrometer on at the 200th s, analyzing the carbon stable isotope ratios of ethanol and glycerol in wines according to the above-mentioned conditions. 2. Oxygen stable isotope ratio analysis: switching a Gasbench instrument on, setting the chromatographic column temperature to 70° C., inflating helium containing 0.3% of $CO_2$ by utilizing an accessory sample injector of the instrument, equilibrating at 28° C. for over 18 hours, and analyzing the oxygen stable isotope ratio of $CO_2$ in the headspace gas as a stable isotope of oxygen in water. 3. Elemental analysis: utilizing an Inductively Coupled Plasma-Mass Spectrometer (ICP-MS) to analyze the element contents in digested wine samples, ICP-MS conditions: power: 1400 W; the flow rate of the atomizer: 0.85 ml/min; the flow rate of cooling gas: 14.2 L/min; the flow rate of auxiliary gas: 0.8 L/min; sampling depth: 150; pulse voltage: 3380 V; and analog voltage: 1800 V.

4) statistical modeling: adopting or utilizing information of the origins of the wine samples and analytical data of step 3) to perform statistical modeling, importing 80% of the information of the origins of the wine samples and the analytical data into a software capable of performing multivariate statistical analysis and modeling, such as SPSS, and modeling analysis is performed regarding the origins utilizing a linear discriminant analysis (LDA) method. A origin discrimination model coefficient matrix and the corresponding predicted accuracy rate of the origin discrimination can be obtained.

5) model verification: grouping the rest 20% data of the wine samples and then importing the data into the model obtained in step 4), providing a predicted grouping information, and calculating the verification precision of the model according to the accuracy rate of the predicted grouping information.

6) sample testing: the origin of an unknown sample can be discriminated by analyzing the above-mentioned discrimination indices, using an unknown sample into in the model, and ultimately determining attributes of the origin, and deeming the accuracy rate of the model verification as the accuracy rate of this origin discrimination.

The method for tracing wine origin based on multielements and stable isotopes provided by the present invention can bring at least the following beneficial effects:

The present invention can be applied to the tracing of wine origin, can be used to discriminate the place of origin of imported and domestic premium wines, and assist import and export inspection department with the origin discrimination of wines. Moreover, in combination with various identification indices, wines from global main wine origins can be differentiated. The index system is optimized, and a database of more than 1000 samples in total from eight global main wine-producing regions (France, Spain, Italy, Chile, South Africa, the USA, Australia and China) is established, and the tracing of the origins of global wines is achieved according to the established discrimination matrix of origins.

In addition, the present invention can achieve the discrimination of the source area of an unknown wine sample by the analysis of the stable isotopes and the element contents in combination with the information database of authentic wine origins; and the accuracy rate and scope of application for the origin determination can be improved with the continuous expansion of the database of the authentic sample origins. The indices measured in this invention are all data that could easily be detected and obtained currently, with a wide applicability and a high data stability, and the discrimination accuracy rate for partial countries reaches 93% in combination with multivariate statistical analysis.

BRIEF DESCRIPTION OF THE DRAWING

In order to more clearly illustrate the technical solutions in the specific embodiments of the present invention or in the prior art, the drawing to be used in the description of the specific embodiments or the prior art will be briefly presented below; and obviously, the drawing in the following description is a certain embodiment of the present invention, and for a person ordinarily skilled in the art, further drawings could be obtained according to the drawing without inventive efforts.

FIG. 1 is a schematic flow diagram of a method for tracing wine origin based on multielements and stable isotopes provided in an embodiment of the present invention.

DETAILED DESCRIPTION OF EMBODIMENTS

In order to make the object, the technical solutions and advantages of the embodiments of the present invention more clear, clear and complete description regarding the technical solutions in the embodiments of the present invention will be made with reference to the drawings in the following contents. Obviously, the described embodiments are merely some but not all embodiments of the present invention. Based on the embodiments in the present invention, all further embodiments that could be obtained by a person ordinarily skilled in the art without inventive efforts fall in the scope of protection of the present invention.

Referring to FIG. 1, the principle of the present invention is as follows: an information database of authentic wine origin is established by the analysis of multiple metallic elements and stable isotopes in wine, and a discrimination model of authentic wine origins is established in combination with multivariate statistical analysis (discriminant analysis), thereby achieving the source area discrimination of an unknown wine sample. More specifically, it comprises the following facts:

1. Wine is made from grapes, and the element distribution in the wine is related to the soil type of the grape planting area. Thus, the contents of the elements can indicate the information about the wine origin.

2. The varieties and types of the grapes from different origins also have significant difference, for example, Cabernet Sauvignon, Merlot and Cabernet Franc are mainly planted in Bordeaux; and Tempranillo is the main variety of grapes in Span etc. Meanwhile, the carbon stable isotope ratios of $CO_2$ in the atmosphere of different origins are also related to the climate and the use of fossil fuels in this region. The above-mentioned circumstances would all possibly result in a difference in the carbon stable isotope ratios in ethanol and glycerol in the wine. Thus, carbon stable isotope ratios can also reflect certain attributes of the origin.

3. Grapes are mainly planted at latitudes of 30-50 degrees north and south, and the difference in latitude and altitude causes a change of oxygen and hydrogen isotope ratios in the rainfall. The isotope D of hydrogen and the isotope $^{18}O$ of oxygen are less in the regions of high latitude and high altitude, which leads to a significant difference in oxygen isotopes in the water of wine between origins.

In the present invention, analysis regarding the carbon stable isotope ratios of ethanol and glycerol in wine, the oxygen stable isotope ratio in water and the content of 16 elements (Ca, K, Mg, Na, B, Al, Sc, Ti, Cr, Mn, Fe, Cu, Zn, Rb, Sr, Ba) is made by collecting standard samples of red wines from main producing regions of the world. A discrimination model for origin is established by utilizing multivariate statistical analysis (linear discriminant analysis) according to the information about the origins of the wine samples, and the discrimination accuracy rate is calculated.

The specific experimental procedures are as follows:

1) sample collection: collecting wine samples from a plurality of origins, wherein the samples collected from each country are not less than 50 in number, and cover the main origins in this region respectively, and a distribution of the origins of authentic samples from different countries in the present invention are shown in Table 1.

2) sample pre-processing: filtering each of the wine samples collected in step 1) using a pore size of 0.22 μm aqueous filter membrane, and pouring 1.5 ml of a filtrate into an autosampler vial for carbon stable isotope ratio analysis of ethanol and glycerol; pouring 0.3 ml of the wine sample into a 12 ml glass tube with stopper for analyzing oxygen stable isotopes in the water; and pouring 0.5 ml of the wine sample into a 15 ml centrifuge tube, and adding 0.5 ml of concentrated $HNO_3$, performing digestion overnight, and diluting to 10 ml to be tested.

3) sample analysis: 1. carbon stable isotope analysis: switching the host machine of a stable isotope ratio mass spectrometer (Thermo Fisher, Delta V advantage) on and adjusting a reference gas balance, such that the variations of the carbon and oxygen stable isotope ratios of ten-group $CO_2$ reference gases are less than 0.06‰. GC conditions: ethanol: a sample injection amount of 0.1 μl, a sample injection port of 250° C., a carrier gas high pure helium, a flow rate of 1.5 ml/min, and a split ratio of 200:1. Programmed temperature-rising conditions: an initial temperature of 40° C., holding for 1 min, and then raising it to 220° C. at a rate of 50° C./min, holding for 3 min. Glycerol: a sample injection amount of 0.2 μl, a sample injection port temperature of 250° C., a carrier gas of high pure helium, a flow rate of 1.5 ml/min, and a split ratio of 20:1. Programmed temperature-rising conditions: an initial temperature of 80° C., holding for 1 min, and then raising it to 240° C. at a rate of 15° C./min, holding for 2 min. Isolink conditions: a combustion tube temperature of 1000° C., and switching the mass spectrometer on at the 200th s, analyzing the carbon stable isotope ratio of ethanol and glycerol in wines according to the above-mentioned conditions. 2. Oxygen stable isotope ratio analysis: switching a Gasbench instrument on, setting the chromatographic column temperature to 70° C., inflating helium containing 0.3% of $CO_2$ by utilizing an accessory sample injector of the instrument, equilibrating at 28° C. for over 18 hours, and analyzing the oxygen stable isotope ratio of $CO_2$ in the headspace gas as a stable isotope of oxygen in water. 3. Elemental analysis: utilizing an Inductively Coupled Plasma-Mass Spectrometer (ICP-MS) to analyze the element contents in digested wine samples, ICP-MS conditions: power: 1400 W; the flow rate of the atomizer: 0.85 ml/min; the flow rate of cooling gas: 14.2 L/min; the flow rate of auxiliary gas: 0.8 L/min; sampling depth: 150; pulse voltage: 3380 V; and analog voltage: 1800 V.

4) statistical modeling: adopting or utilizing information of the origins of the wine samples and analytical data of step 3) to perform statistical modeling, importing 80% of the information of the origins of the wine samples and the analytical data into a software capable of performing multivariate statistical analysis and modeling, such as SPSS, and modeling analysis is performed regarding the origins utilizing a linear discriminant analysis (LDA) method. A origin discrimination model coefficient matrix and the corresponding predicted accuracy rate of the origin discrimination can be obtained.

5) model verification: grouping the rest 20% data of the wine samples and then importing the data into the model obtained in step 4), providing a predicted grouping information, and calculating the verification precision of the model according to the accuracy rate of the predicted grouping information.

6) sample testing: the origin of an unknown sample can be discriminated by analyzing the above-mentioned discrimination indices, using an unknown sample into in the model, and ultimately determining attributes of the origin, and deeming the accuracy rate of the model verification as the accuracy rate of this origin discrimination.

Data 1 Typical Database Structure of Sample Information

In order to better manage the data of the attribute of wines, we utilized a specialized data management software (Access 2013) to manage the wine database, and a database comprising eight sample attributes and the data was established (shown in Table 1). Regarding the attribute of the origins, three levels of origin, that is, country, producing region and producing sub-region, were set, and wines from producing sub-regions can be differentiated. In addition, vintage and grape variety are also important attributes of wines, and the recording of the two indices can provide data support for the identification of vintage and grape variety. The information about wine chateau (wine company) and about the geographic coordinates of the chateau is contributive to the understanding of the regional distribution trend of mineral elements and stable isotopes, and the information of the origin distribution trend of different data can be provided by means of a spatial analysis tool, which facilitates a multi-angle discrimination of a sample.

TABLE 1

Structural Pattern of the Database of Wine Origins

| Items | Attributes |
| --- | --- |
| Sample attributes | Sample number, country, producing region, producing sub-region, vintage, grape variety, wine chateau (company), geographic coordinates |
| Mineral elements | Ca K Mg Na B Al Sc Ti Cr Mn Fe Cu Zn Rb Sr Ba |
| Stable isotopes | $\delta^{13}C$ (ethanol, glycerol), $\delta^{18}O$ in water |

In Table 2, the number of the wine samples and their origin distribution are measured.

Totally 757 effective wine sample data were obtained in the present invention (as shown in Table 2). Since France is a wine-producing country, which has the highest export value of wines in the world, and French wines are the easiest to counterfeit at the same time. Thus, wines from France were intensively sampled in the present invention, wherein totally 240 wines from four producing regions, i.e. Bordeaux, Burgundy, Languedoc-Roussillon and Rhone, were selected, while 517 wines were from other countries. Among the samples, about 80% of the database samples were used to establish a discrimination model, and 20% of the database samples served as verification samples for verifying the accuracy rate of the model discrimination.

TABLE 2

Distribution Information of Origins of the Wine Samples

| Countries | Regions | Amount |
| --- | --- | --- |
| France | Bordeaux | 106 |
|  | Burgundy | 33 |
|  | Languedoc-Roussillon | 57 |
|  | Rhone | 44 |
| Spain |  | 98 |
| Italy |  | 77 |
| US |  | 50 |
| Australia |  | 88 |
| Chile |  | 83 |
| South Africa |  | 55 |
| China |  | 66 |
| Total |  | 757 |

Data 2 Model Discrimination Coefficient Matrix

Utilizing the discriminant analysis method (DA), a discrimination model of origin attributes of different countries was established according to the indices such as mineral elements and stable isotopes. According to the contributions of different indices, six groups of discriminant equations were obtained, and the coefficient matrixes of equations were shown in table 3, from which it could be determined that the indices contributing to the discriminant analysis are ethanol $\delta^{13}C$, $\delta^{18}O$ in water and 11 mineral elements. Six groups of discriminant values can be obtained by respectively substituting the wine analysis data in the database into a corresponding equation.

TABLE 3

Standardized Coefficient Matrixes of Typical Discriminant Functions

| | Functional Matrix | | | | | | |
| --- | --- | --- | --- | --- | --- | --- | --- |
| Variable | Function 1 | Function 2 | Function 3 | Function 4 | Function 5 | Function 6 | Function 7 |
| EN13C | −0.34 | −0.51 | −0.21 | 0.69 | 0.33 | −0.09 | 0.58 |
| GLY13C | −0.04 | 0.43 | 0.37 | −0.29 | 0.07 | 0.06 | −0.05 |
| O18 | 0.30 | 0.65 | 0.11 | 0.41 | 0.03 | 0.57 | −0.03 |
| Ca | 0.31 | −0.25 | −0.24 | −0.06 | 0.78 | 0.35 | −0.06 |

TABLE 3-continued

Standardized Coefficient Matrixes of Typical Discriminant Functions

Functional Matrix

| Variable | Function 1 | Function 2 | Function 3 | Function 4 | Function 5 | Function 6 | Function 7 |
|---|---|---|---|---|---|---|---|
| K | −0.44 | −0.34 | −0.10 | −0.05 | 0.06 | 0.32 | −0.07 |
| Mg | 0.42 | −0.22 | 0.03 | −0.35 | −0.31 | 0.02 | −0.03 |
| Na | 0.44 | 0.11 | 0.28 | −0.36 | 0.10 | −0.29 | 0.40 |
| B | 0.17 | −0.34 | −0.11 | 0.08 | −0.24 | 0.19 | −0.55 |
| Cr | 0.02 | −0.23 | 0.00 | 0.21 | 0.08 | −0.03 | 0.35 |
| Mn | 0.11 | −0.18 | −0.06 | −0.19 | −0.67 | 0.32 | 0.42 |
| Rb | 0.36 | 0.24 | −0.82 | 0.31 | 0.23 | −0.29 | 0.24 |
| Sr | 0.21 | −0.21 | 0.38 | 0.56 | 0.19 | −0.49 | −0.17 |
| Ba | 0.13 | −0.03 | 0.20 | −0.29 | 0.14 | −0.48 | −0.16 |
| Cu | −0.03 | 0.08 | 0.15 | −0.20 | 0.51 | 0.11 | 0.00 |
| Al | −0.18 | −0.24 | −0.02 | 0.02 | −0.32 | 0.34 | 0.01 |
| Fe | −0.56 | 0.38 | −0.10 | −0.27 | 0.12 | −0.34 | −0.10 |
| Zn | 0.05 | 0.26 | 0.12 | 0.04 | 0.09 | 0.08 | 0.31 |
| Sc | −0.05 | 0.38 | −0.02 | −0.28 | −0.16 | 0.10 | −0.23 |
| Ti | −0.13 | 0.27 | 0.13 | 0.04 | −0.18 | −0.23 | −0.18 |

Data 3 Typical Accuracy Rate Analysis of Model Discrimination

Combining the classification accuracy of all the samples, it could be calculated that the overall discrimination accuracy rate of eight countries reaches a level of 82.3% (as shown in Table. 4). Particularly, the discrimination accuracy rates for France and South Africa reach higher than 90%. The discrimination accuracy rates for Spain can reach higher than 80%, while the discrimination accuracy rates for the USA and Italy is relatively poor, and the main reason might be the great difference in the geological conditions and climatic conditions between the producing regions in the two countries, such that various indices lose representativeness due to the great distributive difference. Thus, in a situation where a sample is determined to be wine from these regions, it is necessary to further verify the accuracy of the discrimination. The overall discrimination accuracy rate of the verification samples reaches 80.9%, and the discrimination results of the prediction group are identical to that of the verification group, which indicates that the results predicted by this discrimination model are reliable. Particularly, the discrimination accuracy rates for France and South Africa reach higher than 90%, which indicates that wines from France can be effectively differentiated from wines from other producing regions. Due to the relatively close geographical locations of France, Italy and some producing regions in Spain, misjudgment easily occurs, and more effective differentiation can be achieved in the practical application by eliminating samples from distracting producing regions.

In general, this model can achieve preliminary differentiation between main wine origins in the world, and can discriminate a circumstance in which a wine from a country with a low value counterfeits a wine from a country with a high value. With the continuous improvement of the database, it is expectable that a more accurate discrimination capability can be provided in the aspect of authenticity identification of imported wines.

TABLE 4

Accuracy Rate of Origin Discrimination of Different Countries (%)

| | | prediction group | | | | | | | | | verification group | | | | | | | | |
|---|---|---|---|---|---|---|---|---|---|---|---|---|---|---|---|---|---|---|---|
| | | SA | AU | CH | FR | IT | SP | US | ZH | total | SA | AU | CH | FR | IT | SP | US | ZH | total |
| counting | SA | 39 | 0 | 0 | 0 | 1 | 0 | 2 | 0 | 42 | 10 | 0 | 0 | 0 | 0 | 0 | 0 | 0 | 10 |
| | AU | 6 | 56 | 1 | 0 | 5 | 0 | 3 | 0 | 71 | 1 | 13 | 0 | 0 | 0 | 0 | 2 | 0 | 15 |
| | CH | 2 | 1 | 51 | 3 | 6 | 0 | 2 | 1 | 66 | 0 | 1 | 13 | 0 | 1 | 0 | 0 | 0 | 15 |
| | FR | 1 | 0 | 1 | 151 | 1 | 7 | 2 | 1 | 164 | 0 | 0 | 1 | 36 | 1 | 3 | 0 | 0 | 40 |
| | IT | 0 | 3 | 5 | 6 | 43 | 3 | 1 | 3 | 64 | 0 | 0 | 0 | 4 | 6 | 1 | 1 | 0 | 12 |
| | SP | 0 | 0 | 0 | 10 | 1 | 66 | 2 | 1 | 80 | 0 | 1 | 0 | 2 | 0 | 11 | 0 | 1 | 14 |
| | US | 3 | 1 | 3 | 1 | 1 | 1 | 22 | 1 | 33 | 1 | 1 | 2 | 0 | 0 | 0 | 6 | 0 | 10 |
| | ZH | 0 | 0 | 1 | 3 | 2 | 2 | 1 | 41 | 50 | 0 | 0 | 1 | 0 | 2 | 1 | 0 | 11 | 15 |
| discrimination accuracy rate (%) | SA | 92.9 | 0 | 0 | 0 | 2.4 | 0 | 4.8 | 0 | 100 | 100 | 0 | 0 | 0 | 0 | 0 | 0 | 0 | 100 |
| | AU | 8.5 | 78.9 | 1.4 | 0 | 7 | 0 | 4.2 | 0 | 100 | 6.7 | 80 | 0 | 0 | 0 | 0 | 13.3 | 0 | 100 |
| | CH | 3 | 1.5 | 77.3 | 4.5 | 9.1 | 0 | 3 | 1.5 | 100 | 0 | 6.7 | 86.7 | 0 | 6.7 | 0 | 13.3 | 0 | 100 |
| | FR | 0.6 | 0 | 0.6 | 92.1 | 0.6 | 4.3 | 1.2 | 0.6 | 100 | 0 | 0 | 2.5 | 90 | 2.5 | 0 | 7.5 | 0 | 100 |
| | IT | 0 | 4.7 | 7.8 | 9.4 | 67.2 | 4.7 | 1.6 | 4.7 | 100 | 0 | 0 | 0 | 33.3 | 50 | 8.3 | 8.3 | 0 | 100 |
| | SP | 0 | 0 | 0 | 12.5 | 1.3 | 82.5 | 2.5 | 1.3 | 100 | 0 | 7.1 | 0 | 14.3 | 0 | 78.6 | 0 | 7.1 | 100 |
| | US | 9.1 | 3 | 9.1 | 3 | 3 | 3 | 66.7 | 3 | 100 | 10 | 10 | 20 | 0 | 0 | 0 | 60 | 0 | 100 |
| | ZH | 0 | 0 | 2 | 6 | 4 | 4 | 2 | 82 | 100 | 0 | 0 | 6.7 | 0 | 13.3 | 6.7 | 0 | 73.3 | 100 |

The overall discrimination accuracy rate of the prediction group is 82.3%, while the overall discrimination accuracy rate of the verification group is 80.9%.

Wherein, SA: South Africa; AU: Australia; CH: Chile; FR: France; IT: Italy; SP: Spain; US: United States of America; and ZH: China.

In the depiction in the present description, description made through terms such as "an embodiment" means that specific features, structures, materials or characteristics described in combination with this embodiment or example are included in at least one embodiment or example of the present invention. In the present description, the schematic expression of the above-mentioned terms does not necessarily refer to the same embodiment or example. Moreover, the specific features, structures, materials or characteristics described here can be combined with each other in a suitable way in any one or more embodiments or examples.

The above-mentioned is merely preferable embodiments of the present invention, and is not intended to limit the present invention; and for a person skilled in the art, the present invention may be modified and varied in various ways. Any modifications, equivalent substitutions, and improvements made within the spirit and principle of the present invention shall be covered in the scope of protection of the present invention.

The invention claimed is:

1. A method for tracing wine origin based on multielements and stable isotopes, characterized by comprising steps of:
   1) sample collection: collecting wine samples from a plurality of origins;
   2) sample pre-processing: filtering each of the wine samples collected in Step 1) using a pore size of 0.22 μm aqueous filter membrane, and pouring 1.5 ml of a filtrate into an autosampler vial for carbon stable isotope ratio analysis of ethanol and glycerol; pouring 0.3 ml of the wine sample into a 12 ml glass tube with a stopper for analyzing oxygen stable isotopes in water; and pouring 0.5 ml of the wine sample into a 15 ml centrifuge tube, and adding 0.5 ml of concentrated $HNO_3$, performing digestion overnight, and diluting to a constant volume of 10 ml to be tested;
   3) sample analysis: performing carbon stable isotope analysis, oxygen stable isotope ratio analysis and elemental analysis, respectively;
   4) statistical modeling: utilizing information of the origins of the wine samples and analytical data of Step 3) to perform statistical modeling to obtain a origin discrimination model coefficient matrix and a corresponding predicted accuracy rate of the origin discrimination; and
   5) sample testing: performing origin discrimination by using an unknown sample in the model, and ultimately determining attributes of the origin.

2. The method for tracing wine origin based on multielements and stable isotopes according to claim 1, characterized in that the carbon stable isotope analysis comprises steps of: switching on a host machine of a stable isotope ratio mass spectrometer and adjusting a reference gas balance, such that a variation of the carbon stable isotope ratios of $CO_2$ reference gases is less than 0.06‰.

3. The method for tracing wine origin based on multielements and stable isotopes according to claim 1, characterized in that the elemental analysis is performed by utilizing an Inductively Coupled Plasma-Mass Spectrometer.

4. The method for tracing wine origin based on multielements and stable isotopes according to claim 1, characterized in that the oxygen stable isotope ratio analysis comprises steps of: switching on a Gasbench instrument, setting a chromatographic column temperature to 70° C., inflating helium containing 0.3% of $CO_2$ by utilizing an accessory sample injector of the instrument, equilibrating at 28° C. for over 18 hours, and analyzing the oxygen stable isotope ratio of $CO_2$ in headspace gas as a stable isotope of oxygen in water.

5. The method for tracing wine origin based on multielements and stable isotopes according to claim 1, characterized in that a model verification step is comprised between Step 4) and Step 5), wherein the model verification step comprises steps of: grouping the data of the wine samples and importing the data into the model obtained in Step 4), providing a predicted grouping information, and calculating a verification precision of the model according to the accuracy rate of the predicted grouping information.

* * * * *